US006818655B2

(12) United States Patent
Dhanak et al.

(10) Patent No.: US 6,818,655 B2
(45) Date of Patent: Nov. 16, 2004

(54) UROTENSIN-II RECEPTOR ANTAGONISTS

(75) Inventors: Dashyant Dhanak, King of Prussia, PA (US); Steven D. Knight, King of Prussia, PA (US); Gregory L. Warren, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/470,115

(22) PCT Filed: Jan. 25, 2002

(86) PCT No.: PCT/US02/02007

§ 371 (c)(1),
(2), (4) Date: Jul. 25, 2003

(87) PCT Pub. No.: WO02/058702

PCT Pub. Date: Aug. 1, 2002

(65) Prior Publication Data

US 2004/0063757 A1 Apr. 1, 2004

Related U.S. Application Data

(60) Provisional application No. 60/264,439, filed on Jan. 26, 2001.

(51) Int. Cl.$^7$ .................. A61K 31/47; C07D 215/38
(52) U.S. Cl. .................. 514/313; 546/153; 546/159; 546/163
(58) Field of Search .................. 514/313; 546/153, 546/159, 163

(56) References Cited

U.S. PATENT DOCUMENTS 5,093,333 A  3/1992  Saab
6,075,137 A  6/2000  Culp et al.

FOREIGN PATENT DOCUMENTS

WO  WO 99/55677  11/1999

*Primary Examiner*—Zinna Northington Davis
(74) *Attorney, Agent, or Firm*—Linda E. Hall; Stephen Venetianer; Charles M. Kinzig

(57) ABSTRACT

The present invention relates to quinolines, pharmaceutical compositions containing them and their use as antagonists of urotensin II.

5 Claims, No Drawings

UROTENSIN-II RECEPTOR ANTAGONISTS

CROSS REFERENCES TO RELATED APPLICATIONS

This application is a National Stage Application filed under 35 U.S.C.§371 of PCT/US02/02007, filed on Jan. 25, 2002, which claims priority of U.S. Provisional Application No. 60/264,439, filed Jan. 26, 2001.

FIELD OF THE INVENTION

The present invention relates generally to quinolines, pharmaceutical compositions containing them, and their use as antagonists of urotensin II.

BACKGROUND OF THE INVENTION

The integrated control of cardiovascular homeostasis is achieved through a combination of both direct neuronal control and systemic neurohormonal activation. Although the resultant release of both contractile and relaxant factors is normally under stringent regulation, an aberration in this status quo can result in cardiohemodynamic dysfunction with pathological consequences.

The principal mammalian vasoactive factors that comprise this neurohumoral axis, namely angiotensin-II, endothelin-1, norepinephrine, all function via an interaction with specific G-protein coupled receptors (GPCR). Urotensin-II, represents a novel member of this neurohumoral axis.

In the fish, this peptide has significant hemodynamic and endocrine actions in diverse end-organ systems and tissues:

smooth muscle contraction
  both vascular and non-vascular in origin including smooth muscle preparations from the gastrointestinal tract and genitourinary tract. Both pressor and depressor activity has been described upon systemic administration of exogenous peptide osmoregulation:
  effects which include the modulation of transepithelial ion ($Na^+$, $Cl^-$) transport.
  Although a diuretic effect has been described, such an effect is postulated to be secondary to direct renovascular effects (elevated GFR)

metabolism:
  urotensin-II influences prolactin secretion and exhibits a lipolytic effect in fish (activating triacylglycerol lipase resulting in the mobilization of non-esterified free fatty acids)
  (Pearson, et. al. *Proc. Natl. Acad. Sci.* (U.S.A.) 1980, 77, 5021; Conlon, et. al. *J. Exp. Zool.* 1996, 275, 226.)

In studies with human Urotensin-II it was found that it:
was an extremely potent and efficacious vasoconstrictor
exhibited sustained contractile activity that was extremely resistant to wash out
had detrimental effects on cardiac performance (myocardial contractility)

Human Urotensin-II was assessed for contractile activity in the rat-isolated aorta and was shown to be the most potent contractile agonist identified to date. Based on the in vitro pharmacology and in vivo hemodynamic profile of human Urotensin-II it plays a pathological role in cardiovascular diseases characterized by excessive or abnormal vasoconstriction and myocardial dysfunction. (Ames et. al. *Nature* 1999, 401, 282)

Compounds that antagonize the Urotensin-II receptor may be useful in the treatment of congestive heart failure, stroke, ischemic heart disease (angina, myocardial ischemia), cardiac arrhythmia, hypertension (essential and pulmonary), COPD, restenosis, asthma, (Hay DWP, Luttinann M A, Douglas S A: 2000, Br J Pharmacol: In press.) neurogenic inflammation and metabolic vasculopathies all of which are characterized by abnormal vasoconstriction and/or myocardial dysfunction. Since U-II and GPR14 are both expressed within the mammalian CNS (Ames et. al. *Nature* 1999, 401, 282), they also may be useful in the treatment of addiction, schizophrenia, impulsivity, anxiety, stress, depression, and neuromuscular function. Functional U-II receptors are expressed in rhabdomyosarcomas cell lines and therefore may have oncological indications. Urotensin may also be implicated in various metabolic diseases such as diabetes (Ames et. al. *Nature* 1999, 401, 282, Nothacker et al., *Nature Cell Biology* 1: 383–385, 1999).

SUMMARY OF THE INVENTION

In one aspect this invention provides for quinolines and pharmaceutical compositions containing them.

In a second aspect, this invention provides for the use of quinolines as antagonists of urotensin II, and as inhibitors of urotensin II.

In another aspect, this invention provides for the use of quinolines for treating conditions associated with urotensin II imbalance.

In an yet another aspect, this invention provides for the use of these quinolones analogs for the treatment of congestive heart failure, stroke, ischemic heart disease (angina, myocardial ischemia), cardiac arrhythmia, hypertension (essential and pulmonary), COPD, restenosis, asthma, neurogenic inflammation and metabolic vasculopathies, addiction, schizophrenia, impulsivity, anxiety, stress, depression, neuromuscular function, arthritis and other inflammatory diseases, fibrosis (e.g. pulmonary fibrosis), sepsis, atherosclerosis and dyslipidemiadiabetes, various gastrointestinal dysfunctions such as esophageal reflux and gasthic motility disorders.

The urotensin antagonist may be administered alone or in conjunction with one or more other therapeutic agents, said agents being selected from the group consisting of endothelin receptor antagonists, angiotensin converting enzyme (ACE) inhibitors, vasopeptidase inhibitors, diuretics, digoxin, and dual non-selective $\beta$-adrenoceptor and $\alpha_1$-adrenoceptor antagonists.

Other aspects and advantages of the present invention are described further in the following detailed description of the preferred embodiments thereof.

DETAILED DESCRIPTION OF THE INVENTION

The present invention provides for compounds of Formula I:

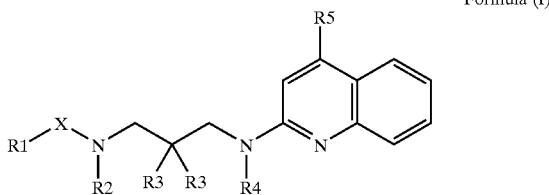

Formula (I)

wherein:
R$_1$ is 1,1-diphenylmethyl, 1,1-diphenylethyl, xanthyl, phenyl, benzimidazolyl, thiophenyl, 3-indolyl, or 2-indolyl, all of which may be substituted or unsubstituted by one, two, or three halogen, C$_{1-6}$ alkoxy, C$_{1-6}$ alkyl, benzenesulfonyl, trifluoromethyl, or trifluoromethylthio groups or they may be substituted by a benzyl, which is further substituted or unsubstituted by one, two, or three halogen, C$_{1-6}$ alkoxy, or C$_{1-6}$ alkyl groups;

R$_2$ is hydrogen or C$_{1-3}$alkyl;

R$_3$ is independently hydrogen, C$_{1-6}$ alkyl, phenyl, or benzyl, wherein the phenyl or benzyl may be substituted or unsubstituted by a methylenedioxy group, or one or two halogens, C$_{1-3}$alkyl; or C$_{1-3}$alkoxy groups;

or both R$_3$ groups together with the carbon they are attached to is a C$_{3-7}$cycloalkyl group;

R$_4$ is hydrogen or C$_{1-3}$alkyl;

R$_5$ is hydrogen, C$_{1-3}$alkoxy, or CONR$_6$R$_7$;

R$_6$ is hydrogen or C$_{1-6}$ alkyl;

R$_7$ is hydrogen or C$_{1-6}$ alkyl;

or R$_6$ and R$_7$ together with the nitrogen they are attached to form a 5 or 6 membered ring;

X is —CR$_8$R$_9$ or C═O;

R$_8$ is hydrogen or C$_{1-3}$alkyl;

R$_9$ is hydrogen or C$_{1-3}$alkyl;

or R$_8$ and R$_9$ together with the carbon they are attached to form a C$_{5-6}$cycloalkyl group;

or a pharmaceutically acceptable salt thereof.

When used herein, the term "alkyl" and similar terms such as "alkoxy" includes all straight chain and branched isomers. Representative examples thereof include methyl, ethyl, n-propyl, iso-propyl, n-butyl, sec-butyl, iso-butyl, t-butyl, n-pentyl and n-hexyl.

When used herein, the terms 'halogen' and 'halo' include fluorine, chlorine, bromine and iodine and fluoro, chloro, bromo and iodo, respectively.

The compounds of the present invention may contain one or more asymmetric carbon atoms and may exist in racemic and optically active form. All of these compounds and their diastereoisomers are contemplated to be within the scope of the present invention.

R$_1$ is preferably 1,1-diphenylmethyl, xanthyl, phenyl, thiophenyl, 3-indolyl, or 2-indolyl, substituted or unsubstituted by one, two, or three halogen, methoxy, methyl, benzenesulfonyl, trifluoromethyl, or trifluoromethylthio groups, or benzyl, substituted or unsubstituted by one, two, or three halogen groups.

R$_2$ preferably is hydrogen.

R$_3$ preferably is hydrogen, C$_{1-3}$ alkyl, or phenyl or benzyl; or R$_3$ together with the carbon they are attached to, is a C$_{5-6}$ cycloalkyl group.

R$_4$ preferably is hydrogen.

R$_5$ preferably is methoxy or CONR$_6$R$_7$.

R$_6$ preferably is hydrogen or C$_{1-3}$ alkyl.

R$_7$ preferably is hydrogen or C$_{1-3}$ alkyl.

X preferably is CH$_2$ or C═O.

Preferred Compounds are:

N-(1-benzyl-1H-indol-3-ylmethyl)-N'-(4-methoxyquinolin-2-yl)propane-1,3-diamine;

N-(4,5-Dibromothiophen-2-ylmethyl)-N'-(4-methoxyquinolin-2-yl)propane-1,3-diamine;

N-(1-Benzyl-1H-indol-3-ylmethyl)-N'-(4-methoxyquinolin-2-yl)-2-propylpropane-1,3-diamine;

N-(1-Benzyl-1H-indol-3-ylmethyl)-N'-(4-methoxyquinolin-2-yl)-N,N'-dimethylpropane-1,3-diamine;

N-(1-Benzyl-1H-indol-3-ylmethyl)-N'-(4-methoxyquinolin-2-yl)-2-phenylpropane-1,3-diamine;

N-(1-Benzyl-1H-indol-2-ylmethyl)-N'-(4-methoxyquinolin-2-yl)propane-1,3-diamine;

N-(1H-Benzoimidazol-2-ylmethyl)-N'-(4-methoxyquinolin-2-yl)propane-1,3-diamine;

N'-(1-Benzyl-1H-indol-3-ylmethyl)-N-(4-methoxyquinolin-2-yl)-N-methylpropane-1,3-diamine;

(R)-N-(1-Benzyl-1H-indol-3-ylmethyl)-N'-(4-methoxyquinolin-2-yl)-2-propylpropane-1,3-diamine;

(S)-N-(1-Benzyl-1H-indol-3-ylmethyl)-N'-(4-methoxyquinolin-2-yl)-2-propylpropane-1,3-diamine;

N-(1-Benzyl-1H-indol-3-ylmethyl)-N,N '-dimethyl-N'-quinolin-2-yl-propane-1,3-diamine;

N-(1-Benzyl-1H-indol-3-ylmethyl)-N'-quinolin-2-yl-propane-1,3-diamine;

N-(1-Benzenesulfonyl-1H-indol-3-ylmethyl)-N'-quinolin-2-yl-propane-1,3diamine;

(R)-N-(1-Benzyl-1H-indol-3-ylmethyl)-N'-(4-methoxyquinolin-2-yl)-2-phenylpropane-1,3-diamine;

(S)-N-(1-Benzyl-1H-indol-3-ylmethyl)-N'-(4-methoxyquinolin-2-yl)-2-phenylpropane-1,3-diamine;

N-(1H-Indol-3-ylmethyl)-N'-(4-methoxyquinolin-2-yl)propane-1,3-diamine;

2-Benzo[1,3]dioxol-5-ylmethyl-N-(1-benzyl-1H-indol-3-ylmethyl)-N'-(4-methoxyquinolin-2-yl)propane-1,3-diamine;

N-(1-Benzenesulfonyl-1H-indol-3-ylmethyl)-N'-(4-methoxy-quinolin-2-yl)-propane-1,3-diamine;

1-Benzyl-4,6-dichloro-1H-indole-2-carboxylic acid [3-(4-methoxy-quinolin-2-ylamino)-propyl]-amide;

4,6-Dichloro-1H-indole-2-carboxylic acid [3-(4-methoxyquinolin-2-ylanino)propyl]amide;

N-(4,6-Dichloro-1H-indol-2-ylmethyl)-N'-(4-methoxyquinolin-2-yl)propane-1,3-diamine;

1-Benzyl-1-H-indole-3-carboxylic acid [3-(4-methoxy-quinolin-2-ylamino)-propyl]-amide;

N-[3-(4-Methoxy-quinolin-2-ylamino)-propyl]-2,2-diphenyl-acetamide;

N-(2,2-Diphenyl-ethyl)-N'-(4-methoxy-quinolin-2-yl)-propane-1,3-diamine;

N-[1-(3,5-Dibromobenzyl)-1H-indol-3-ylmethyl]-N'-(4-methoxyquinolin-2-yl)propane-1,3-diamine;

N-[2,2-Bis-(4-chlorophenyl)-ethyl]-N-(4-methoxy-quinolin-2-yl)-propane-1,3-diamine;

2-Benzyl-N-(1-benzyl-1H-indol-3-ylmethyl)-N'-(4-methoxy-quinolin-2-yl)-propane-1,3-diamine;

N-(1-Benzyl-H-indol-3-ylmethyl)-N'-(4-methoxy-quinolin-2-yl)-2-methyl-propane-1,3-diamine;

(1-{[(1-Benzyl-1H-indol-3-ylmethyl)-amino]-methyl}-cyclohexylmethyl)-(4-methoxy-quinolin-2-yl)-amine;

N-(1-Benzyl-1H-indol-3-ylmethyl)-N'-(4-methoxy-quinolin-2-yl)-2,2-dimethyl-propane-1,3-diamine;

2,2-Bis-(4-chlorophenyl)-N-[3-(4-methoxy-quinolin-2-ylamino)-propyl]-acetamide;

9H-Xanthene-9-carboxylic acid [3-(4-methoxy-quinolin-2-ylamino)-propyl]-amide;

2-[3-(3,4-Dichloro-benzylamino)-propylamino]-quinoline-4-carboxylic acid dimethylamide;

2-{3-[(4,6-Dichloro-1H-indol-2-ylmethyl)-amino]-propylamino}-quinoline-4-carboxylic acid dimethylamide;

2-[3-(4-Chloro-3-trifluoromethyl-benzylamino)-propylamino]-quinoline-4-carboxylic acid dimethylamide; and 2-[3-(4-Chloro-3-trifluoromethyl-benzylamino)-propylamino]-quinoline-4-carboxylic acid methylamide.

Most Preferred Compounds are:

N-(1-benzyl-1H-indol-3-ylmethyl)-N'-(4-methoxyquinolin-2-yl)propane-1,3diamine;

2-[3-(4-Chloro-3-trifluoromethyl-benzylamino)-propylamino]-quinoline-4-carboxylic acid dimethylamide;

2-[3-(4-Chloro-3-trifluoromethyl-benzylamino)-propylamino]-quinoline-4-carboxylic acid methylamide;

N-(1-Benzyl-1H-indol-3-ylmethyl)-N'-(4-methoxyquinolin-2-yl)-2-propylpropane-1,3-diamine;

N-(1-Benzyl-H-indol-3-ylmethyl)-N'-(4-methoxyquinolin-2-yl)-2-phenylpropane-1,3-diamine;

N-(1-Benzenesulfonyl-1H-indol-3-ylmethyl)-N'-(4-methoxy-quinolin-2-yl)-propane-1,3-diamine;

N-(1-Benzyl-1H-indol-3-ylmethyl)-N'-(4-methoxyquinolin-2-yl)-2-methylpropane-1,3-diamine.

Compounds of Formula (I) may be prepared as outlined in the following scheme:

Scheme 1

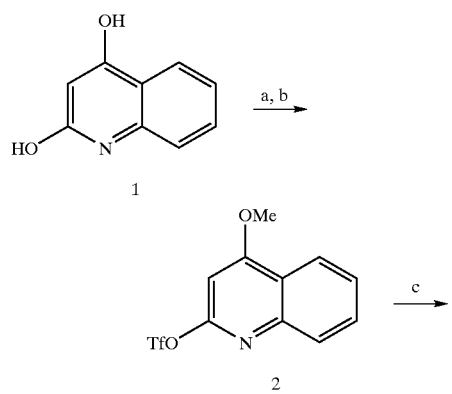

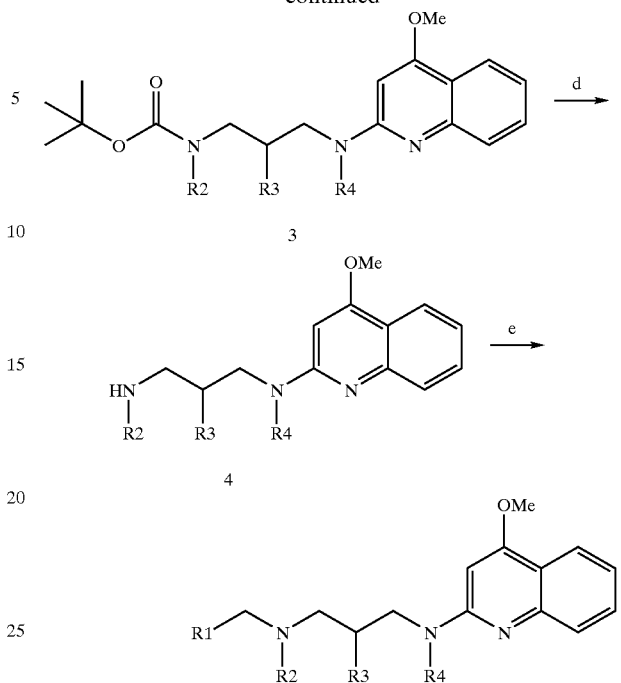

Conditions: a) Dimethylsulfate, methylene chloride, acetone, reflux; b) trifluoroacetic anhydride, pyridine, rt; c) BocR$_2$NCH$_2$CHR$_3$CH$_2$NHR$_4$, acetonitrile, diisopropylethylamine, reflux; d) 4 N hydrochloric acid in dioxane, rt; e) R$_1$CHO, acetic acid, sodium methoxide, methanol, rt, then sodium cyanoborohydride. (R$_1$, R$_2$, R$_3$, and R$_4$ are as defined above.)

Methylation of 2,4-dihydroxyquinoline (1) with dimethylsulfate, followed by treatment with trifluoroacetic anhydride furnished intermediate 2, as outlined in Scheme 1. Coupling of 2 with various mono-tert-butoxycarbonyl protected propylenediamines was accomplished in acetonitrile at reflux to give urethanes 3. Removal of the tert-butoxycarbonyl protecting group with 4 N hydrochloric acid in dioxane, followed by reductive alkylation of the resultant amines 4 with various aldehydes provided the target compounds 5.

Alternatively, 1-(3-dimethylaminopropyl)-3-ethylcarbodiimide hydrochloride mediated coupling of amines 4 with various carboxylic acids gave amides 6, as outlined in Scheme 2. Reduction of the amide carbonyl with borane-tetrahydrofuran also furnished amines 5.

Scheme 2

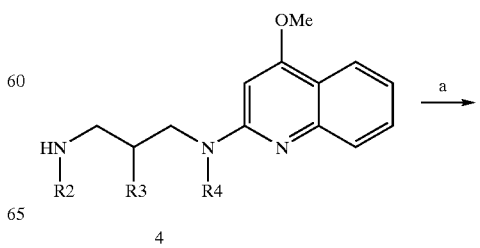

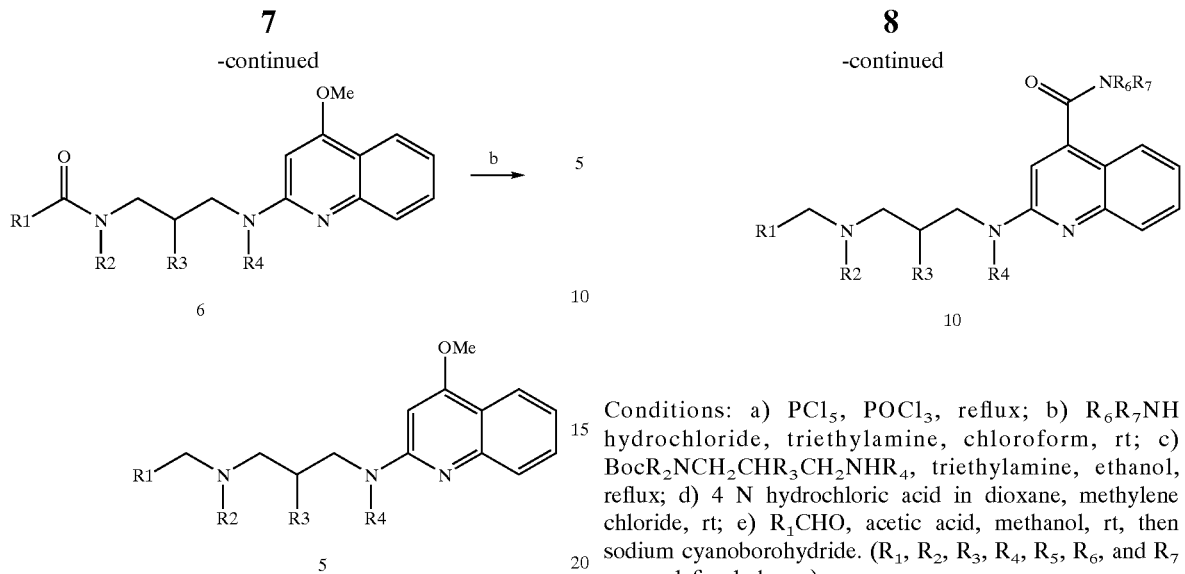

Conditions: a) $R_1COOH$, 1-(3-dimethylaminopropyl)-3-ethylcarbodiimide hydrochloride, 1-hydroxybenzotriazole hydrate, N-methylmorpholine, N,N-dimethylformamide, rt; b) borane in tetrahydrofuran, reflux. ($R_1$, $R_2$, $R_3$, and $R_4$ are as defined above.)

Compounds of Formula (I) where $R_5$ is an optionally substituted carboxamide may be prepared as outlined in Scheme 3.

Conditions: a) $PCl_5$, $POCl_3$, reflux; b) $R_6R_7NH$ hydrochloride, triethylamine, chloroform, rt; c) $BocR_2NCH_2CHR_3CH_2NHR_4$, triethylamine, ethanol, reflux; d) 4 N hydrochloric acid in dioxane, methylene chloride, rt; e) $R_1CHO$, acetic acid, methanol, rt, then sodium cyanoborohydride. ($R_1$, $R_2$, $R_3$, $R_4$, $R_5$, $R_6$, and $R_7$ are as defined above.)

Treatment of hydroxyacid 7 with phosphorus pentachloride and phosphorus oxychloride, followed by reaction with various amines furnished amides 8. Coupling of 8 with various mono-tert-butoxycarbonyl protected propylenediamines was accomplished in ethanol at reflux, followed by removal of the tert-butoxycarbonyl protecting group with 4 N hydrochloric acid in dioxane to provide amines 9. Reductive alkylation of the resultant amines 9 with various aldehydes provided the target compounds 10.

Compounds of Formula (I) where $R_3$=methyl may be prepared as outlined in Scheme 4.

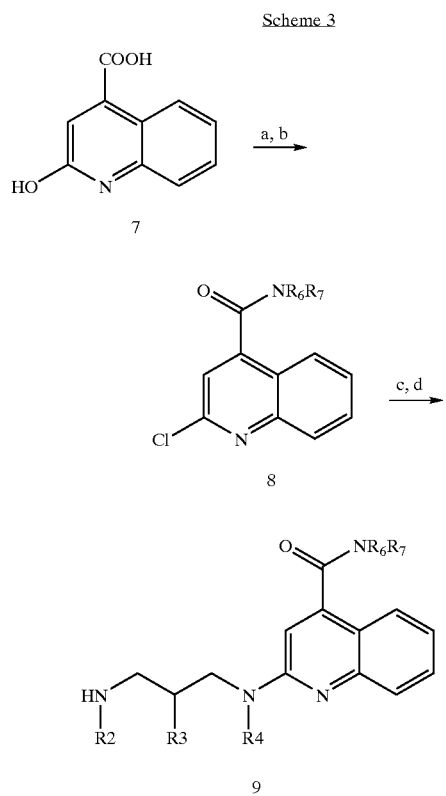

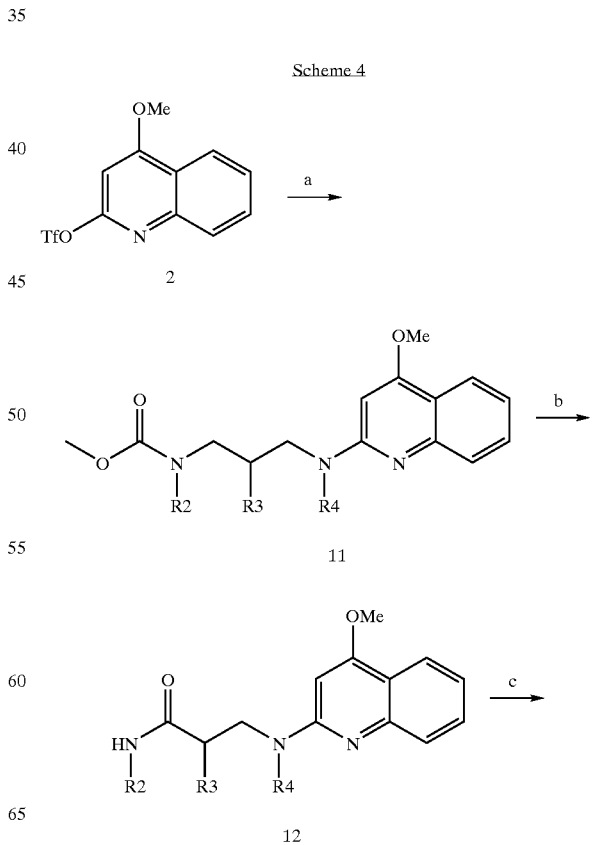

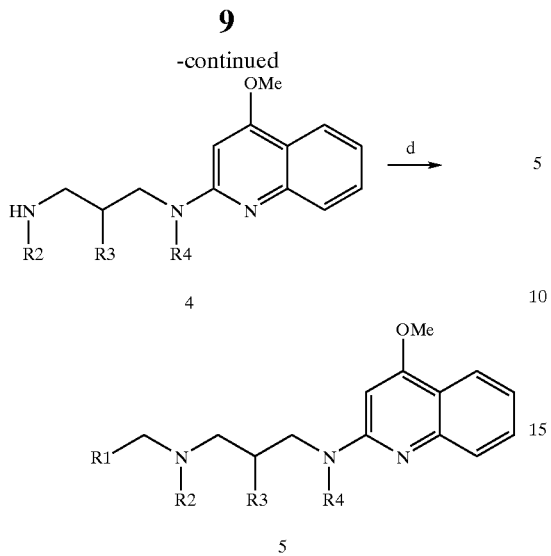

4

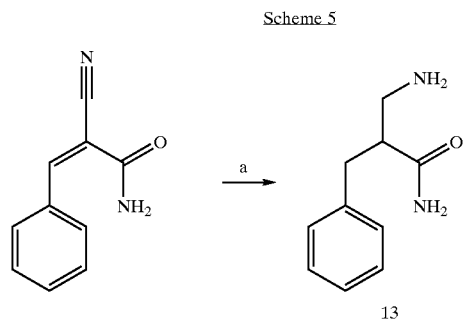

5

Conditions: a) 3-amino-2-methyl-propionic acid methyl ester, acetonitrile, diisopropylethyl amine, reflux; b) trimethylaluminum, ammonium chloride, methylene chloride, rt; c) borane in tetrahydrofuran, reflux; d) $R_1CHO$, acetic acid, sodium methoxide, methanol, rt, then sodium cyanoborohydride. ($R_1$, $R_2$, $R_3$, and $R_4$ are as defined above.)

Coupling of 2 with 3-amino-2-methyl-propionic acid methyl ester(Adams et al. *J. Chem. Soc.*, 1959, 3061) was accomplished in acetonitrile at reflux to give urethane 11. Conversion of ester 11 to amide 12 using trimethylaluminum followed by borane reduction afforded amine 4. Reductive alkylation of amine 4 as described in Scheme 1 (step e) provided the target compound 5.

Compounds of Formula (I) where $R_3$=benzyl may be prepared as outlined in Scheme 5.

Scheme 5

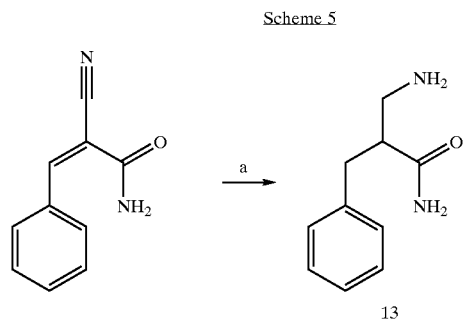

Conditions: a) $H_2$, palladium on carbon, ethanol, hydrochloric acid

Amide 13 was prepared from (E)-2-cyano-3-phenyl-acrylamide (purchased from Bionet) via hydrogenation. Coupling of 2 with amide 13 was accomplished in acetonitrile at reflux to give urethane 12, which was subsequently converted to the target compound 5 as described in Scheme 4 (steps c and d).

Compounds of Formula (I) where $R_3$=cyclohexyl may be prepared as outlined in Scheme 6.

Scheme 6

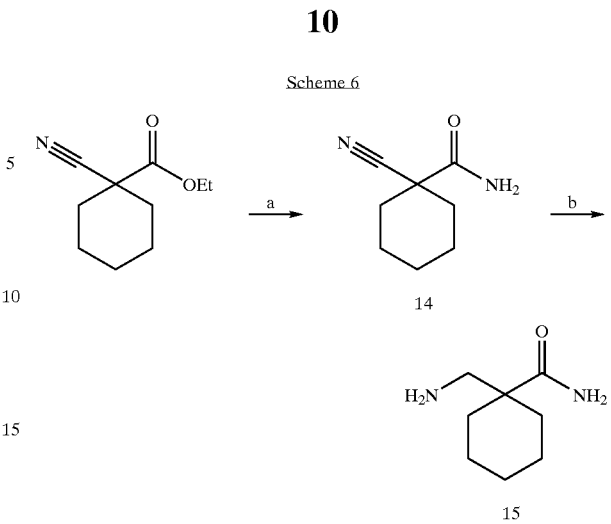

Conditions: a) Ammonia, rt; b) hydrogen, palladium on carbon, ethanol, hydrochloric acid Conversion of 1-cyano-cyclohexanecarboxylic acid ethyl ester (Julia et al., *Bull Soc. Chim. Fr.* 1969, 2427) to the corresponding amide using ammonia gas followed by hydrogenation provided amide 15. Coupling of 2 with amide 15 was accomplished in acetonitrile at reflux to give urethane 12, which was subsequently converted to the target compound 5 as described in Scheme 4 (steps c and d).

Scheme 7

Compounds of Formula (I) where $R_3$ = phenyl may be prepared as outlined in Scheme 7.

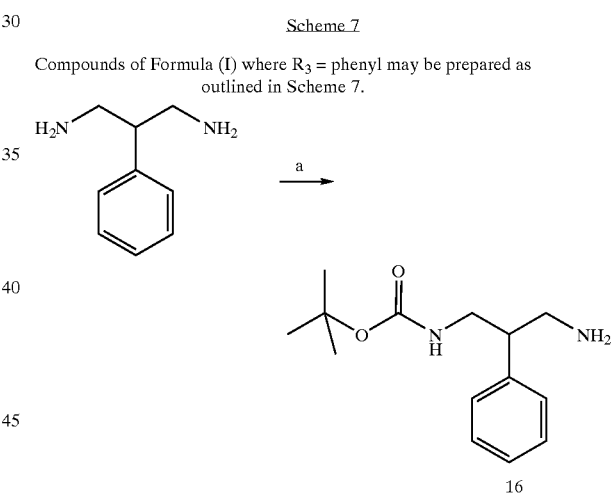

Conditions: a) Di-tert-butyl dicarbonate, tetrahydrofuran, rt

Mono-protection of 2-phenyl-propane-1,3-diamine (Weinhardt et al. *J. Med. Chem.*, 1985, 28, 694) afforded amine 16. Coupling of 2 with amine 16 was accomplished in acetonitrile at reflux to give urethane 12, which was subsequently converted to the target compound 5 as described in Scheme 4 (steps c and d).

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

These quinoline analogs may be used for the treatment of congestive heart failure, stroke, ischemic heart disease (angina, myocardial ischemia), cardiac arrhythmia, hypertension (essential and pulmonary), COPD, restenosis, asthma, neurogenic inflammation and metabolic vasculopathies, addiction, schizophrenia, impulsivity, anxiety, stress, depression, neuromuscular function, and diabetes.

The urotensin antagonist may be administered alone or in conjunction with one or more other therapeutic agents, said agents being selected from the group consisting of endothelin receptor antagonists, angiotensin converting enzyme (ACE) inhibitors, vasopeptidase inhibitors, diuretics, digoxin, and dual non-selective β-adrenoceptor and $\alpha_1$-adrenoceptor antagonists.

No unacceptable toxicological effects are expected when compounds of the invention are administered in accordance with the present invention.

The biological activity of the compounds of Formula (I) are demonstrated by the following tests:

Radioligand Binding

HEK-293 cell membranes containing stable cloned human and rat GPR-14 (20 ug/assay) were incubated with 200 pM [125I] h-U-II (200 Ci/mmol$^{-1}$ in the presence of increasing concentrations of test compounds in DMSO (0.1 nM to 10 uM), in a final incubation volume of 200 ul (20 mM Tris-HCl, 5 mM MgCl2). Incubation was done for 30 minutes at room temperature followed by filtration GF/B filters with Brandel cell harvester. $^{125}$I labeled U-II binding was quantitated by gamma counting. Nonspecific binding was defined by $^{125}$I U-II binding in the presence of 100 nM of unlabeled human U-II. Analysis of the data was performed by nonlinear least square fitting.

$Ca^{2+}$-mobilization

A microtitre plate based $Ca^{2+}$-mobilization FLIPR assay (Molecular Devices, Sunnyvale, Calif.) was used for the functional identification of the ligand activating HEK-293 cells expressing (stable) recombinant GPR-14. The day following transfection, cells were plated in a poly-D-lysine coated 96 well black/clear plates. After 18–24 hours the media was aspirated and Fluo 3AM-loaded cells were exposed to various concentrations (10 nM to 30 uM) of test compounds followed by h-U-II. After initiation of the assay, fluorescence was read every second for one minute and then every 3 seconds for the following one minute. The inhibitory concentration at 50% (IC50)was calculated for various test compounds.

Inositol Phosphates Assays

HEK-293-GPR14 cells in T150 flask were prelabeled overnight with 1 uCi myo-[$^3$H] inositol per ml of inositol free Dulbecco's modified Eagel's medium. After labeling, the cells were washed twice with Dulbecco's phosphate-buffered saline (DPBS) and then incubated in DPBS containing 10 mM LiCl for 10 min at 37° C. The experiment was initiated by the addition of increasing concentrations of h-U-II (1 pM to 1 $\mu$M ) in the absence and presence of three different concentrations (0.3, 1 and 10 uM) of test compounds and the incubation continued for an additional 5 min at 37° C. after which the reaction was terminated by the addition of 10% (final concentration) trichloroacetic acid and centrifugation. The supernatants were neutralized with 100 ul of 1M Trizma base and the inositol phosphates were separated on AG 1-X8 columns (0.8 ml packed, 100–200 mesh) in formate phase. Inositol monophosphate was eluted with 8 ml of 200 mM ammonium formate. Combined inositol di and tris phosphate was eluted with 4 ml of 1M ammonium formate/0.1 M formic acid. Eluted fractions were counted in beta scintillation counter. Based on shift from the control curve KB was calculated.

Activity for the compounds of this invention range from (radioligand binding assay): Ki=1 nM -10000 nM [e.g. Ki (example 29)=90 nM]

EXAMPLE 1

Preparation of N-(1-benzyl-1H-indol-3-ylmethyl)-N'-(4-methoxyquinolin-2-yl)propane-1,3-diamine a) 2-Hydroxy-4-methoxyquinoline A slurry of 2,4-dihydroxyquinoline (20.7 g, 0.13 mol), potassium carbonate (35.5 g, 0.26 mol), and dimethyl sulfate (14.6 ml, 0.15 mol) in acetone (800 ml) was heated at reflux for 3 days. The reaction was cooled to ambient temperature then evaporated under reduced pressure. The residue was slurried in a system of water (1000 ml) and ethyl acetate (500 ml) for 1 hour. The solids were collected then rinsed with water (3×250 ml) and ethyl ether (3×250 ml). Vacuum dried over phosphorus pentoxide to give 2-hydroxy4-methoxyquinoline (16.3 g, 72%) as a tan powder. [M+H]+ 176, M+CH$_3$CN=217.

b) 1,1,1-Trifluoromethanesulfonic Acid 4-Methoxyquinolin-2-yl Ester

A slurry of 2-hydroxy-4-methoxyquinoline (13.4 g, 76.6 mmol) in pyridine (75 ml) was slowly treated under argon with trifluoromethanesulfonic anhydride (15.5 ml, 91.2 mmol). The reaction was allowed to stir at ambient temperature. After 4 days, the reaction was evaporated under reduced pressure to an oil that was azeotroped from toluene (2×200 ml) to give the crude product as a brown solid. Flash chromatography on silica (1:1 ethyl acetate/hexanes as eluent) gave 1 1,1-trifluoromethanesulfonic acid 4-methoxyquinolin-2-yl ester (20.4 g, 87%) as a yellow oil that solidified on standing. [M+H]+ 308, M+CH$_3$CN=349.

c) [3-(4-Methoxyquinolin-2-ylamino)propyl]carbamic Acid Tert-butyl Ester

A solution of 1,1,1-trifluoromethanesulfonic acid 4-methoxyquinolin-2-yl ester (4.51 g, 14.7 mmol), tert-butyl N-(3-aminopropyl)carbamate (3.07 g, 17.6 mmol), and diisopropylethylamine (3.84 ml, 22.0 mmol) in anhydrous acetonitrile (35 ml) was heated at reflux for 6 days. The solution was cooled to ambient temperature then evaporated under reduced pressure to an oil. It was taken into water (35 ml) then extracted into ethyl acetate. The extracts were dried (sodium sulfate) then concentrated to an oil. Column chromatography on silica (1:1 ethyl acetate/hexanes) gave [3-(4-methoxyquinolin-2-ylamino)propyl]carbamic acid tert-butyl ester (3.10 g, 64%) as a colorless oil that solidified on standing. [M+H]+ 332.

d) N'-(4-Methoxyquinolin-2-yl)propane-1,3-diamine Dihydrochloride

A solution of [3-(4-methoxyquinolin-2-ylamino)propyl] carbamic acid tert-butyl ester (3.10 g, 9.35 mmol) in anhydrous dichloromethane (20 ml) was treated with 4N HCl in 1,4-dioxane (10 ml). It was stirred at ambient temperature for 2 hours then was evaporated under reduced pressure to give N'-(4-methoxyquinolin-2-yl)propane-1,3-diamine dihydrochloride (2.81 g, 99%) as a white solid. [M+H]+ 232.

e) N-(1-Benzyl-1H-indol-3-ylmethyl)-N'-(4-methoxyquinolin-2-yl)propane-1,3-diamine A solution of N'-(4-methoxyquinolin-2-yl)propane-1,3-diamine dihydrochloride (200 mg, 0.66 mmol) [4a] in methanol (50 ml) was treated with glacial acetic acid (20 drops) and sodium methoxide (95%, 71 mg, 1.31 mmol) followed by a solution of 1-benzyl-3-indole carboxaldehyde (155 mg, 0.66 mmol) in methanol (5.0 ml). The reaction stirred at ambient temperature for 24 hours then was treated with a solution of sodium cyanoborohydride (83 mg, 1.31 mmol) in methanol (2.0 ml). The reaction stirred at ambient temperature for 24 hours. The solution was evaporated under reduced pressure to a residue that was taken into a mixture of saturated aqueous sodium chloride (20 ml) and 10% sodium hydroxide solution (20 ml). It was extracted in ethyl acetate and the extracts were dried (sodium sulfate) then concentrated to an oil. Column chromatography on silica (95/5 dichloromethane/methanolic ammonia) gave N-(1-benzyl-1H-indol-3-ylmethyl)-N'-(4-methoxyquinolin-2-yl) propane-1,3-diamine (126 mg, 84%) as a white solid. [M+H]+ 451.

Compounds derived from Scheme 1:

| Example | Compound | MS (ES+) m/e [M + H]+ |
|---|---|---|
| 2 | N-(4,5-Dibromothiophen-2-ylmethyl)-N'-(4-methoxyquinolin-2-yl)propane-1,3-diamine | 486 |
| 3 | N-(1-Benzyl-1H-indol-3-ylmethyl)-N'-(4-methoxyquinolin-2-yl)-2-propylpropane-1,3-diamine | 493 |
| 4 | N-(1-Benzyl-1H-indol-3-ylmethyl)-N'-(4-methoxyquinolin-2-yl)-N,N'-dimethylpropane-1,3-diamine | 479 |
| 5 | N-(1-Benzyl-1H-indol-3-ylmethyl)-N'-(4-methoxyquinolin-2-yl)-2-phenylpropane-1,3-diamine | 527 |
| 6 | N-(1-Benzyl-1H-indol-2-ylmethyl)-N'-(4-methoxyquinolin-2-yl)propane-1,3-diamine | 451 |
| 7 | N-(1H-Benzoimidazol-2-ylmethyl)-N'-(4-methoxyquinolin-2-yl)propane-1,3-diamine | 362 |
| 8 | N'-(1-Benzyl-1H-indol-3-ylmethyl)-N-(4-methoxyquinolin-2-yl)-N-methylpropane-1,3-diamine | 465 |
| 9 | (R)-N-(1-Benzyl-1H-indol-3-ylmethyl)-N'-(4-methoxyquinolin-2-yl)-2-propylpropane-1,3-diamine | 493 |
| 10 | (S)-N-(1-Benzyl-1H-indol-3-ylmethyl)-N'-(4-methoxyquinolin-2-yl)-2-propylpropane-1,3-diamine | 493 |
| 11 | N-(1-Benzyl-1H-indol-3-ylmethyl)-N,N'-dimethyl-N'-quinolin-2-yl-propane-1,3-diamine | 449 |
| 12 | N-(1-Benzyl-1H-indol-3-ylmethyl)-N'-quinolin-2-yl-propane-1,3-diamine | 421 |
| 13 | N-(1-Benzenesulfonyl-1H-indol-3-ylmethyl)-N'-quinolin-2-yl-propane-1,3-diamine | 471 |
| 14 | (R)-N-(1-Benzyl-1H-indol-3-ylmethyl)-N'-(4-methoxyquinolin-2-yl)-2-phenylpropane-1,3-diamine | 527 |

-continued

Compounds derived from Scheme 1:

| Example | Compound | MS (ES+) m/e [M + H]+ |
|---|---|---|
| 15 | (S)-N-(1-Benzyl-1H-indol-3-ylmethyl)-N'-(4-methoxyquinolin-2-yl)-2-phenylpropane-1,3-diamine | 527 |
| 16 | N-(1H-Indol-3-ylmethyl)-N'-(4-methoxyquinolin-2-yl)propane-1,3-diamine | 361 |
| 17 | 2-Benzo[1,3]dioxol-5-ylmethyl-N-(1-benzyl-1H-indol-3-ylmethyl)-N'-(4-methoxyquinolin-2-yl)propane-1,3-diamine | 585 |
| 18 | N-(1-Benzenesulfonyl-1 H-indol-3-ylmethyl)-N'-(4-methoxy-quinolin-2-yl)-propane-1,3-diamine | 501 |
| 19 | N-(1-Benzyl-1H-indol-3-ylmethyl)-N'-(4-methoxyquinolin-2-yl)-2-methylpropane-1,3-diamine | 465 |
| 20 | (1-{[(1-Benzyl-1H-indol-3-ylmethyl)amino]methyl}cyclohexylmethyl)-(4-methoxyquinolin-2-yl)amine | 519 |
| 21 | N-[1-(3,5-Dibromobenzyl)-1H-indol-3-ylmethyl]-N'-(4-methoxyquinolin-2-yl)propane-1,3-diamine | 609 |
| 22 | N-(1-Benzyl-1H-indol-3-ylmethyl)-N'-(4-methoxy-quinolin-2-yl)-2,2-dimethyl-propane-1,3-diamine | 479 |

EXAMPLE 23

Preparation of 1-Benzyl4,6-dichloro-1H-indole-2-carboxylic Acid [3-(4-methoxy-quinolin-2-ylamino)-propyl]-amide.

A solution of $N^1$-(4-methoxyquinolin-2-yl)propane-1,3-diamine dihydrochloride (193 mg, 0.63 mmol) [from example 1d], 1-benzyl4,6-dichloro-1H-indole-2-carboxylic acid (203 mg, 0.63 mmol), 1-(3-dimethylaminopropyl)-3-ethylcarbodiimide hydrochloride (182 mg, 0.95 mmol), 1-hydroxybenzotriazole hydrate (94 mg, 0.70 mmol), and N-methylmorpholine (244 μl, 2.22 mmol) in anhydrous N,N-dimethylformamide (5 ml) was stirred for 2 days. The resulting slurry was taken into water (50 ml) and 10% sodium hydroxide solution (10 ml). Extracted into ethyl acetate. The extracts were dried (sodium sulfate) and evaporated to an oil. Column chromatography on silica (2:1 ethyl acetate/hexanes) gave 1-benzyl-4,6-dichloro-1H-indole-2-carboxylic acid [3-(4-methoxy-quinolin-2-ylamino)-propyl]-amide (269 mg, 80%) as a white solid. [M+H]+ 533.

EXAMPLE 24

Synthesis of N-(1-Benzyl-4,6-dichloro-1H-indol-2-ylmethyl)-N'-(4-methoxyquinolin-2-yl)propane-1,3-diamine Dihydrochloride.

A solution of 1-benzyl-4,6-dichloro-1H-indole-2-carboxylic acid [3-(4-methoxy-quinolin-2-ylamino)-propyl]-amide (200 mg, 0.37 mmol) [from example 12] in anhydrous tetrahydrofuran (15 ml) was treated with 1 N borane-tetrahydrofuran complex (1.1 ml, 1.1 mmol). The solution was heated a reflux for 24 hours then cooled to ambient temperature. Treated with the dropwise addition of concentrated hydrochloric acid (1 ml) then stirred for 1 hour. Evaporated under reduced pressure to a residue and taken into a system of saturated aqueous sodium chloride (20 ml) and 10% sodium hydroxide (20 ml). Extracted into ethyl acetate. The extracts were dried (sodium sulfate) then evaporated to an oil. Column chromatography on silica (95/5 methylene chloride/methanolic ammonia) gave N-(1-benzyl-4,6-dichloro-1H-indol-2-ylmethyl)-N'-(4-methoxyquinolin-2-yl)propane-1,3-diamine as a colorless resin. This was taken into chloroform (5 ml) then treated with 4N hydrogen chloride in 1,4-dioxane (300 μl). Evaporation under reduced pressure gave N-(1-benzyl-4,6-dichloro-1H-indol-2-ylmethyl)-N'-(4-methoxyquinolin-2-yl)propane-1,3-diamine dihydrochloride (102 mg, 42%) as a white solid. [M+H]+ 519.

Compounds derived from Scheme 2:

| Example | Compound | MS (ES+) m/e [M + H]+ |
|---|---|---|
| 25 | 1-Benzyl-4,6-dichloro-1H-indole-2-carboxylic acid [3-(4-methoxy-quinolin-2-ylamino)-propyl]-amide | 533 |
| 26 | 4,6-Dichloro-1H-indole-2-carboxylic acid [3-(4-methoxyquinolin-2-ylamino)propyl]amide | 443 |
| 27 | N-(4,6-Dichloro-1H-indol-2-ylmethyl)-N'-(4-methoxyquinolin-2-yl)propane-1,3-diamine | 429 |
| 28 | 1-Benzyl-1-H-indole-3-carboxylic acid [3-(4-methoxy-quinolin-2-ylamino)-propyl]-amide | 465 |
| 29 | N-[3-(4-Methoxy-quinolin-2-ylamino)-propyl]-2,2-diphenyl-acetamide | 426 |
| 30 | N-(2,2-Diphenyl-ethyl)-N'-(4-methoxy-quinolin-2-yl)-propane-1,3-diamine | 412 |
| 31 | 9H-Xanthene-9-carboxylic acid [3-(4-methoxy-quinolin-2-ylamino)-propyl]-amide | 440 |

-continued

Compounds derived from Scheme 2:

| Example | Compound | MS (ES+) m/e [M + H]+ |
|---|---|---|
| 32 | N-[2,2-Bis-(4-chlorophenyl)-ethyl]-N'-(4-methoxy-quinolin-2-yl)-propane-1,3-diamine | 480 |
| 33 | 2,2-Bis-(4-chlorophenyl)-N-[3-(4-methoxy-quinolin-2-ylamino)-propyl]-acetamide | 494 |

EXAMPLE 34

Synthesis of 2-[3-(4-Chloro-3-trifluoromethylbenzylamino)propylamino]quinoline-4-carboxylic Acid Dimethylamide.

a) 2-Choroquinoline-4-carboxylic Acid Dimethylamide.

A slurry of 2-hydroxyquinoline-4-carboxylic acid (3.0 g, 15.9 mmol), phosphorus pentachloride (3.5 g, 16.7 mmol), and phosphorus oxychloride (20 ml) was heated at reflux for 18 hours. The reaction was then cooled to ambient temperature and evaporated under reduced pressure to a black tar. Residue was dissolved in diethyl ether (100 ml) and washed with ice-cold water and ice-cold brine. Dried over anhydrous sodium sulfate and activated charcoal. Filtration through Celite, followed by evaporation under reduced pressure gave 2-chloroquinoline-4-carbonyl chloride as a light green-gray powder.

A solution of the resultant 2-chloroquinoline-4-carbonyl chloride in chloroform (50 ml) was treated with triethylamine (4.4 ml, 31.5 mmol), followed by solid dimethylamine hydrochloride (1.28 g, 15.7 mmol). The reaction stirred for one hour at ambient temperature at which time it was washed with 10% aqueous sodium hydroxide and 15% aqueous citric acid. Drying over anhydrous sodium sulfate, followed by evaporation under reduced pressure gave 2-chloroquinoline-4-carboxylic acid dimethylamide (1.5 g, 40%) as a tan solid. [M+H]+ 235.

b) 2-(3-Aminopropylamino)quinoline-4-carboxylic Acid Dimethylamide Dihydrochloride A solution of 2-chloroquinoline-4-carboxylic acid dimethylamide (512 mg, 2.18 mmol), tert-butyl N-(3-aminopropyl)carbamate (571 μl, 3.27 mmol), and triethylamine (608 μl, 4.36 mmol) in absolute ethanol (35 ml) was heated at reflux for 7 days. The reaction was then allowed to cool to ambient temperature and was evaporated under reduced pressure to give a yellow oil. The residue was purified by column chromatography (ethyl acetate), dissolved in methylene chloride (10 mL), and treated with 4 N hydrogen chloride in dioxane (3 mL). The reaction was maintained at ambient temperature for 24 hours. Evaporation under reduced pressure gave 2-(3-aminopropylamino) quinoline-4-carboxylic acid dimethylamide dihydrochloride (218 mg, 30%) as a pale yellow solid. [M+H]+ 273.

c) 2-[3-(4-Chloro-3-trifluoromethylbenzylamino) propylamino]quinoline-4-carboxylic Acid dimethylamide dihydrochloride Following the procedure of 1e, except substituting 2-(3-aminopropylamino)quinoline-4-carboxylic acid dimethylamide dihydrochloride (50 mg, 0.14 mmol) for N$^1$-(4-methoxyquinolin-2-yl)propane-1,3-diamine dihydrochloride, 2-[3-(4-Chloro-3-trifluoromethylbenzylamino)propylamino]quinoline-4-carboxylic acid dimethylamide (35 mg, 47%) was obtained as a colorless oil. [M+H]+ 465.

| Example | Compound | MS (ES+) m/e [M + H]+ |
|---|---|---|
| 35 | 2-[3-(3,4-Dichloro-benzylamino)-propylamino]-quinoline-4-carboxylic acid dimethylamide | 431 |
| 36 | 2-{3-[(4,6-Dichloro-1H-indol-2-ylmethyl)-amino]-propylamino}-quinoline-4-carboxylic acid dimethylamide | 471 |
| 37 | 2-[3-(4-Chloro-3-trifluoromethylbenzyl-amino)-propylamino]quinoline-4-carboxylic acid methylamide | 451 |

EXAMPLE 38

Synthesis of N-(1-Benzyl-1H-indol-3-ylmethyl)-N'-(4-methoxy-guinolin-2-yl)-2-methyl-propane-1,3-diamine a) 3-(4-Methoxy-quinolin-2-ylamino)-2-methyl-propionic Acid Methyl Ester A solution of 1,1,1-trifluoromethanesulfonic acid 4-methoxyquinolin-2-yl ester [from Example 1b] (2.03 g, 6.61 mmol) and 3-amino-2-methyl-propionic acid methyl ester (1.5 eq, 1.52 g, 9.91 mmol) in acetonitrile (25 mL) was heated at reflux for five days. It was cooled to room temperature and evaporated to an oil. The crude product was purified via column chromatography on silica (1:1 ethyl acetate/hexane) to give the product (0.75 g, 42%) as an orange oil. [M+H]+ 275.

b) 3-(4-Methoxy-quinolin-2-ylamino)-2-methyl-propionamide

A slurry of ammonium chloride (0.38 g, 7.11 mmol) in dry methylene chloride (20 mL) at 0° C. was treated with trimethylaluminum (1 eq, 7.11 mmol, 3.6 mL of a 2M solution in toluene). The mixture was allowed to warm to room temperature over a period of two hours, at which time a solution of 3-(4-methoxy-quinolin-2-ylamino)-2-methyl-propionic acid methyl ester (0.33 eq, 2.37 mmol, 0.65 g) in dry methylene chloride (5 mL) was added. The solution stirred at room temperature for two hours, then was quenched slowly by addition of concentrated HCl (1 mL). After stirring for an additional 30 minutes, the mixture was diluted with 10% NaOH (30 mL) and brine (20 mL) and extracted into methylene chloride. The organic extracts were dried over $Na_2SO_4$, filtered and concentrated to an oil. Purification via column chromatography on silica (95:5 methylene chloride/methanolic ammonia) provided the product (0.29 g, 48%) as a white solid. $[M+H]^+$ 260.

c) N-(1-Benzyl-1H-indol-3-ylmethyl)-N'-(4-methoxy-quinolin-2-yl)-2-methyl-propane-1,3-diamine Following the procedures of Example 24 and Example 1e, except substituting 3-(4-methoxy-quinolin-2-ylamino)-2-methyl-propionamide for 1-benzyl-4,6-dichloro-1H-indole-2-carboxylic acid [3-(4-methoxy-quinolin-2-ylamino)-propyl]-amide, the title compound was prepared as a white solid (0.23, 49%). [M+H]+ 465.

EXAMPLE 39

Synthesis of N-(1-Benzyl-1H-indol-3-ylmethyl)-N'-(4-methoxy-quinolin-2-yl)-2-benzyl-propane-1,3-diamine a) 3-Amino-2-benzyl-propionamide A solution of (E)-2cyano-3-phenyl-acrylamide (0.50 g, 2.91 mmol) was dissolved in ethanol (25 mL). Concentrated HCl (1 mL) was added, followed by 10% degussa palladium on carbon (1.0 g). The mixture was subjected to hydrogenation conditions (55 psi) for 24 hours. It was filtered through Celite and concentrated to give the product (0.62 g, 100%) as a white solid. [M+H]+ 179.

b) 2-Benzyl-3-(4-methoxy-quinolin-2-ylamino)-propionamide

Following the procedure of Example 1c, except substituting 3-amino-2-benzyl-propionamide for tert-butyl N-(3-aminopropyl)carbamate, the product (0.13 g, 28%) was obtained as a white solid. $[M+H]^+$ 336.

c) 2-Benzyl-N'-(4-methoxy-quinolin-2-yl)-propane-1,3-diamine

Following the procedure of Example 24, except substituting 2-benzyl-3-(4-methoxy-quinolin-2-ylamino)-propionamide for 1-benzyl-4,6-dichloro-1H-indole-2-carboxylic acid [3-(4-methoxy-quinolin-2-ylamino)-propyl]-amide, the product (0.12 g, 100%) was obtained as a colorless oil. $[M+H]^+$ 322.

d) N-(1-Benzyl-1H-indol-3-ylmethyl)-N'(4-methoxy-quinolin-2-yl)-2-benzyl-propane-1,3-diamine Following the procedure of Example 1e, except substituting 2-benzyl-N'-(4-methoxy-quinolin-2-yl)-propane-1,3-diamine for N'-(4-methoxyquinolin-2-yl)propane-1,3-diamine, the title compound (0.03 g, 15%) was obtained as a white solid. $[M+H]^+$ 541.

EXAMPLE 40

Synthesis of (1-{[(1-Benzyl-1H-indol-3-ylmethyl)-amino]methyl}-cyclohexylmethyl)-(4-methoxy-guinolin-2-yl)-amine a) 1-Cyano-cyclohexanecarboxylic Acid Amide 1-Cyano-cyclohexanecarboxylic acid ethyl ester (11.4 g, 63.0 mmol) was placed into a glass pressure vessel and cooled to −78° C. It was charged with ammonia via needle until the total volume had doubled. The vessel was sealed and allowed to stir at room temperature for 20 hours. The solvent was evaporated and the resulting slurry triturated with ethyl acetate. The solids were collected by filtration and then filtered through a silica funnel (50 g silica), washing with ethyl acetate. The filtrate was concentrated to give the product (2.51 g, 26%) as a white solid. $[M+H]^+$ 153.

b) 1-Aminomethyl-cyclohexanecarboxylic Acid Amide Hydrochloride

A solution of 1-cyano-cyclohexanecarboxylic acid amide (2.34 g, 20.0 mmol) in ethanol (50 mL) was treated with concentrated HCl (3 mL) and 10% degussa palladium on carbon (0.50 g). The mixture was subjected to hydrogenation conditions (50 psi) for 24 hours, then filtered through Celite. The filtrate was concentrated, then azeotroped with methanol to give a viscous oil. The oil was then resubjected to the above hydrogenation conditions for an additional 20 hours. It was filtered and concentrated as above to give the product (3.85 g, 100%) as a white solid. $[M+H]^+$ 157.

c) 1-[(4-Methoxy-quinolin-2-ylamino)-methyl]-cyclobexanecarboxylic Acid Amide

Following the procedure of Example 1c, except substituting 1-aminomethyl-cyclohexanecarboxylic acid amide hydrochloride for tert-butyl N-(3-aminopropyl)carbamate, the, product (2.11 g, 59%) was obtained as a white solid. $[M+H]^+$ 314.

d) (1-Aminomethyl-cyclohexylmethyl)-(4-methoxy-quinolin-2-yl)amine

Following the procedure of Example 24, except substituting 1-[(4-methoxy-quinolin-2-ylamino)-methyl]-cyclohexanecarboxylic acid amide for 1-benzyl-4,6-dichloro-1H-indole-2-carboxylic acid [3-(4-methoxy-quinolin-2-ylamino)-propyl]-amide, the product (2.10 g, 97%) was obtained as a yellow solid. $[M+H]^+$ 300.

e) (1-{[(1-Benzyl-1H-indol-3-ylmethyl)-amino]methyl}-cyclohexylmethyl)-(4-methoxy-quinolin-2-yl)-amine Following the procedure of Example 1e, except substituting (1-aminomethyl-cyclohexylmethyl)-(4-methoxy-quinolin-2-yl)-amine for N'-(4-methoxyquinolin-2-yl) propane-1,3-diamine, the title compound (0.05 g, 20%) was obtained as a pale yellow powder. $[+H]^+$ 519.

EXAMPLE 41

Synthesis of N-(1-Benzyl-1H-indol-3-ylmethyl)-N'-(4-methoxy-guinolin-2-yl)-2-phenyl-propane-1,3-diamine a) (3-Amino-2-phenyl-propyl)-carbamic Acid Tert-butyl Ester A solution of 2-phenyl-propane-1,3-diamine (2.20 g, 14.7 mmol) in dry tetrahydrofuran (70 mL) was cooled to 0° C. and treated over 30 minutes with a solution of di-tert-butyl dicarbonate (0.33 eq, 4.88 mmol, 1.10 g) in dry tetrahydrofuran (20 mL). The mixture was allowed to warm to room temperature, stirring overnight. The thick slurry was then concentrated to a white residue, taken into water, and extracted into ethyl acetate. The organic extracts were washed with brine (2×), dried over $Na_2SO_4$, filtered, and concentrated to a colorless oil (1.16 g, 95%). $[M+H]^+$ 251.

b) [3-(4-Methoxy-quinolin-2-ylamino)-2-phenyl-propyl]-carbamic Acid Tert-butyl Ester Following the procedure of Example 1c, except substituting (3-amino-2-phenyl-propyl)-carbamic acid tert-butyl ester for tert-butyl N-(3-aminopropyl)carbamate, the product (0.54 g, 38%) was obtained as a white foamy solid. $[M+H]^+$ 408.

c) N-(1-Benzyl-1H-indol-3-ylmethyl)-N'-(4-methoxy-quinolin-2-yl)-2-phenyl-propane-1,3-diamine Following the procedures of Example 1d and 1e, except substituting [3-(4-methoxy-quinolin-2-ylamino)-2-phenyl-propyl]-carbamic acid tert-butyl ester for N'-(4-methoxyquinolin-2-yl)propane-1,3-diamine, the title compound (0.15 g, 60%) was obtained as a white solid. $[M+H]^+$ 527.

EXAMPLE 42

Formulations for pharmaceutical use incorporating compounds of the present invention can be prepared in various forms and with numerous excipients. Examples of such formulations are given below.

| Tablets/Ingredients | Per Tablet |
|---|---|
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Inhalant Formulation

A compound of Formula I, (1 mg to 100 mg) is aerosolized from a metered dose inhaler to deliver the desired amount of drug per use.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then sterilized by filtration through a 0.22 micron membrane filter and sealed in sterile containers.

The above specification and Examples fully disclose how to make and use the compounds of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound of Formula I:

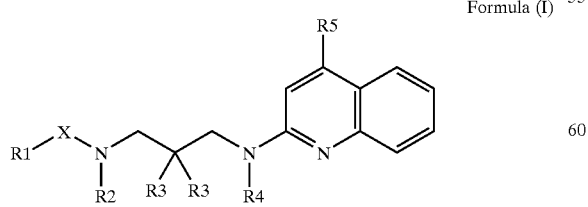

Formula (I)

wherein:

$R_1$ is 1,1-diphenylmethyl, 1,1-diphenylethyl, xanthyl, phenyl, benzimidazolyl, thiophenyl, 3-indolyl, or 2-indolyl, all of which may be substituted or unsubstituted by one, two, or three halogen, $C_{1-6}$ alkoxy, $C_{1-6}$ alkyl, benzenesulfonyl, trifluoromethyl, or trifluoromethylthio groups or they may be substituted by a benzyl, which is further substituted or unsubstituted by one, two, or three halogen, $C_{1-6}$ alkoxy, or $C_{1-6}$ alkyl groups;

$R_2$ is hydrogen or $C_{1-3}$alkyl;

$R_3$ is independently hydrogen, $C_{1-6}$ alkyl, phenyl, or benzyl, wherein the phenyl or benzyl may be substituted or unsubstituted by a methylenedioxy group, or one or two halogens, $C_{1-3}$alkyl; or $C_{1-3}$alkoxy groups;

or both $R_3$ groups together with the carbon they are attached to is a $C_{3-7}$cycloalkyl group;

$R_4$ is hydrogen or $C_{1-3}$alkyl;

$R_5$ is hydrogen, $C_{1-3}$alkoxy, or $CONR_6R_7$;

$R_6$ is hydrogen or $C_{1-6}$ alkyl;

$R_7$ is hydrogen or $C_{1-6}$ alkyl;

or $R_6$ and $R_7$ together with the nitrogen they are attached to form a 5 or 6 membered ring;

X is $-CR_8R_9$ or $C=O$;

$R_8$ is hydrogen or $C_{1-3}$alkyl;

$R_9$ is hydrogen or $C_{1-3}$alkyl;

or $R_8$ and $R_9$ together with the carbon they are attached to form a $C_{5-6}$cycloalkyl group;

or a pharmaceutically acceptable salt thereof.

2. A compound of claim 1 wherein $R_1$ is 1,1-diphenylmethyl, xanthyl, phenyl, thiophenyl, 3-indolyl, or 2-indolyl, substituted or unsubstituted by one, two, or three halogen, methoxy, methyl, benzenesulfonyl, trifluoromethyl, or trifluoromethylthio groups, or benzyl, substituted or unsubstituted by one, two, or three halogen groups; $R_2$ is hydrogen; $R_3$ is hydrogen, $C_{1-3}$ alkyl, or phenyl or benzyl; or $R_3$ together with the carbon they are attached to, is a $C_{5-6}$ cycloalkyl group; $R_4$ is hydrogen; $R_5$ is methoxy or $CONR_6R_7$; $R_6$ is hydrogen or $C_{1-3}$ alkyl; $R_7$ is hydrogen or $C_{1-3}$ alkyl; and X is $CH_2$ or $C=O$.

3. A compound of claim 1 chosen from the group consisting of:

N-(1-benzyl-1H-indol-3-ylmethyl)-N'-(4-methoxyquinolin-2-yl)propane-1,3-diamine;

N-(4,5-Dibromothiophen-2-ylmethyl)-N'-(4-methoxyquinolin-2-yl)propane-1,3-diamine;

N-(1-Benzyl-1H-indol-3-ylmethyl)-N'-(4-methoxyquinolin-2-yl)-2-propylpropane-1,3-diamine;

N-(1-Benzyl-1H-indol-3-ylmethyl)-N'-(4-methoxyquinolin-2-yl)-N,N'-dimethylpropane-1,3-diamine;

N-(1-Benzyl-1H-indol-3-ylmethyl)-N'-(4-methoxyquinolin-2-yl)-2-phenylpropane-1,3-diamine;

N-(1-Benzyl-1H-indol-2-ylmethyl)-N'-(4-methoxyquinolin-2-yl)propane-1,3-diamine;

N-(1H-Benzoimidazol-2-ylmethyl)-N'-(4-methoxyquinolin-2-yl)propane-1,3-diamine;

N'-(1-Benzyl-1H-indol-3-ylmethyl)-N-(4-methoxyquinolin-2-yl)-N-methylpropane-1,3-diamine;

(R)-N-(1-Benzyl-1H-indol-3-ylmethyl)-N'-(4-methoxyquinolin-2-yl)-2-propylpropane-1,3-diamine;

(S)-N-(1-Benzyl-1H-indol-3-ylmethyl)-N'-(4-methoxyquinolin-2-yl)-2-propylpropane-1,3-diamine;

N-(1-Benzyl-1H-indol-3-ylmethyl)-N,N '-dimethyl-N'-quinolin-2-yl-propane-1,3-diamine;

N-(1-Benzyl-1H-indol-3-ylmethyl)-N'-quinolin-2-yl-propane-1,3-diamine;

N-(1-Benzenesulfonyl-1H-indol-3-ylmethyl)-N'-quinolin-2-yl-propane-1,3-diamine;

(R)-N-(1-Benzyl-1H-indol-3-ylmethyl)-N'-(4-methoxyquinolin-2-yl)-2-phenylpropane-1,3-diamine;

(S)-N-(1-Benzyl-1H-indol-3-ylmethyl)-N'-(4-methoxyquinolin-2-yl)-2-phenylpropane-1,3-diamine;

N-(1H-Indol-3-ylmethyl)-N'-(4-methoxyquinolin-2-yl)propane-1,3-diamine;

2-Benzo[1,3]dioxol-5-ylmethyl-N-(1-benzyl-1H-indol-3-ylmethyl)-N'-(4-methoxyquinolin-2-yl)propane-1,3-diamine;

N-(1-Benzenesulfonyl-1H-indol-3-ylmethyl)-N'-(4-methoxy-quinolin-2-yl)-propane-1,3-diamine;

1-Benzyl-4,6-dichloro-1H-indole-2-carboxylic acid [3-(4-methoxy-quinolin-2-ylamino)-propyl]-amide;

4,6-Dichloro-1H-indole-2-carboxylic acid [3-(4-methoxyquinolin-2-ylamino)propyl]amide;

N-(4,6-Dichloro-1H-indol-2-ylmethyl)-N'-(4-methoxyquinolin-2-yl)propane-1,3-diamine;

1-Benzyl-1-H-indole-3-carboxylic acid [3-(4-methoxy-quinolin-2-ylamino)-propyl]-amide;

N-[3-(4-Methoxy-quinolin-2-ylamino)-propyl]-2,2-diphenyl-acetamide;

N-(2,2-Diphenyl-ethyl)-N'-(4-methoxy-quinolin-2-yl)-propane-1,3-diamine;

N-[1-(3,5-Dibromobenzyl)-1H-indol-3-ylmethyl]-N'-(4-methoxyquinolin-2-yl)propane-1,3-diamine;

N-[2,2-Bis-(4-chlorophenyl)-ethyl]-N'-(4-methoxy-quinolin-2-yl)-propane-1,3-diamine;

2-Benzyl-N-(1-benzyl-1H-indol-3-ylmethyl)-N'-(4-methoxy-quinolin-2-yl)-propane-1,3-diamine;

N-(1-Benzyl-1H-indol-3-ylmethyl)-N'-(4-methoxy-quinolin-2-yl)-2-methyl-propane-1,3-diamine;

(1-{[(1-Benzyl-1H-indol-3-ylmethyl)-amino]-methyl}-cyclohexylmethyl)-(4-methoxy-quinolin-2-yl)-amine;

N-(1-Benzyl-1H-indol-3-ylmethyl)-N'-(4-methoxy-quinolin-2-yl)-2,2-dimethyl-propane-1,3-diamine;

2,2-Bis-(4-chlorophenyl)-N-[3-(4-methoxy-quinolin-2-ylamino)-propyl]-acetamide;

9H-Xanthene-9-carboxylic acid [3-(4-methoxy-quinolin-2-ylamino)-propyl]-amide;

2-[3-(3,4-Dichloro-benzylamino)-propylamino]-quinoline-4-carboxylic acid dimethylamide;

2-{3-[(4,6-Dichloro-1H-indol-2-ylmethyl)-amino]-propylamino}-quinoline-4-carboxylic acid dimethylamide;

2-[3-(4-Chloro-3-trifluoromethyl-benzylamino)-propylamino]-quinoline-4-carboxylic acid dimethylamide; and 2-[3-(4-Chloro-3-trifluoromethyl-benzylamino)-propylamino]-quinoline-4-carboxylic acid methylamide.

4. A compound of claim 3 chosen from the group consisting of:

N-(1-benzyl-1H-indol-3-ylmethyl)-N'-(4-methoxyquinolin-2-yl)propane-1,3-diamine;

2-[3-(4-Chloro-3-trifluoromethyl-benzylamino)-propylamino]-quinoline-4-carboxylic acid dimethylamide;

2-[3-(4-Chloro-3-trifluoromethyl-benzylamino)-propylamino]-quinoline-4-carboxylic acid methylamide;

N-(1-Benzyl-1H-indol-3-ylmethyl)-N'-(4-methoxyquinolin-2-yl)-2-propylpropane-1,3-diamine;

N-(1-Benzyl-1H-indol-3-ylmethyl)-N'-(4-methoxyquinolin-2-yl)-2-phenylpropane-1,3-diamine;

N-(1-Benzenesulfonyl-1H-indol-3-ylmethyl)-N'-(4-methoxy-quinolin-2-yl)-propane-1,3-diamine;

N-(1-Benzyl-1H-indol-3-ylmethyl)-N'-(4-methoxyquinolin-2-yl)-2-methylpropane-1,3-diamine.

5. A pharmaceutical composition comprising a compound of claim 1 and a pharmaceutically acceptable carrier.

* * * * *